United States Patent [19]

Shenier

[11] 4,181,818
[45] Jan. 1, 1980

[54] PERSONAL AMPLIFIER SYSTEM

[75] Inventor: Richard S. Shenier, Forest Hills, N.Y.

[73] Assignee: Gentex Corporation, Carbondale, Pa.

[21] Appl. No.: 739,270

[22] Filed: Nov. 5, 1976

[51] Int. Cl.² .............................................. H04M 1/19
[52] U.S. Cl. ................................... 179/1 P; 179/1 G; 179/1 VL; 179/107 FD
[58] Field of Search ........... 179/1 P, 1 A, 1 G, 1 VL, 179/107 FD, 1 HF, 1 CN; 325/303; 318/561

[56] References Cited

U.S. PATENT DOCUMENTS

| | | | |
|---|---|---|---|
| 2,290,992 | 7/1942 | Peterson | 325/303 |
| 3,057,960 | 9/1962 | Kaiser | 179/1 P |
| 3,238,304 | 3/1966 | Yaita | 179/1 G |
| 3,361,971 | 1/1968 | Eaves | 325/303 |
| 3,509,289 | 4/1970 | Briskey | 330/299 |
| 3,725,583 | 4/1973 | Gunderson et al. | 179/1 G |
| 3,755,625 | 8/1973 | Mastin | 179/1 CN |
| 3,893,038 | 7/1975 | Omata et al. | 179/1 G |
| 3,952,158 | 4/1976 | Kyle et al. | 179/1 P |
| 3,992,584 | 11/1976 | Dugan | 179/1 VL |
| 3,995,113 | 11/1976 | Tani | 179/1 P |
| 4,006,427 | 2/1977 | Nishikawa | 179/1 G |
| 4,021,612 | 5/1977 | Takahashi | 179/1 GQ |

OTHER PUBLICATIONS

J. O'Connell et al., "Stereophonic Signal Compression System", RCA TN No. 400, 1960.

Primary Examiner—Thomas W. Brown
Assistant Examiner—E. S. Kemely
Attorney, Agent, or Firm—Shenier & O'Connor

[57] ABSTRACT

A personal amplifier system wherein sound attenuating ear defenders provided with earphones ideally exclude all airborne sound and permit only electronically reproduced sound to be heard. A pair of spaced microphones are coupled to the earphones through amplifying channels, the gains of which are synchronously varied preferably in response to the greater of the output signals of the two channels.

12 Claims, 4 Drawing Figures

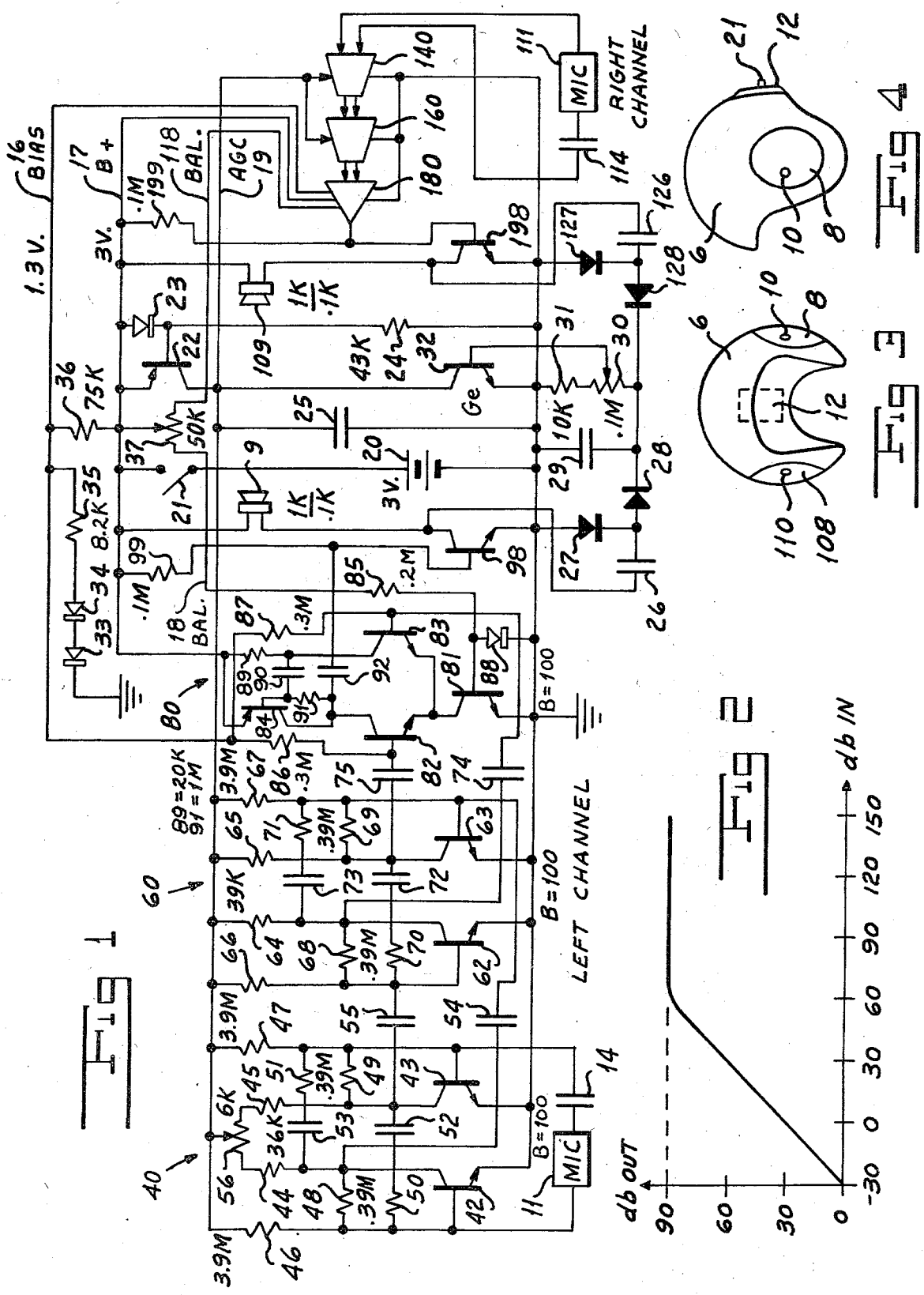

PERSONAL AMPLIFIER SYSTEM

BACKGROUND OF THE INVENTION

The human ear can accommodate sound intensities ranging from approximately 0 db, which is the threshold of audibility to approximately 120 db, which is the threshold of pain. I have provided a personal amplifier system in which sounds varying over a considerably broader range of intensities, such as from −30 db to +150 db are electronically reproduced at the ear with intensities conveniently ranging from 0 db to 90 db. My personal amplifier system is extremely useful in low noise environments, where an effective reduced threshold of audibility would permit faint sounds readily to be heard. My system is also useful in high noise environments, since the effective increased threshold of pain permits the loudest sounds to be heard without physical discomfort. My personal amplifier system employs a pair of channels, one for the left ear and one for the right ear, each including a microphone, a variable gain amplifier, and an earphone. The gains of the amplifiers are synchronously varied, preferably in response to the greater output signal of either channel, over a range of 90 db, while preserving a differential variation of less than 1 db, so that the direction from which even a most intense sound emanates can readily be localized.

SUMMARY OF THE INVENTION

One object of my invention is to provide a personal amplifier system wherein sound attenuating ear defenders provided with earphones ideally exclude all airborne sound and permit only electronically reproduced sound to be heard.

Another object of my invention is to provide a personal amplifier system wherein a pair of spaced microphones are coupled to the earphones through amplifying channels, the gains of which are synchronously varied over a wide range while preserving an extremely small differential variation.

Still another object of my invention is to provide a personal amplifier system wherein the gains of the amplifying channels are synchronously varied in response to the greater of the output signals of the two channels.

A further object of my invention is to provide a variable gain amplifier system including a balanced differential amplifier.

Still a further object of my invention is to provide a variable gain transistor amplifier system including a balanced collector-coupled differential amplifier.

A still further object of my invention is to provide a variable gain amplifier system including a junction transistor biased at the knee of its collector characteristic which defines the edge of the saturation region.

A still further object of my invention is to provide a balanced, variable gain, differential, transistor amplifier system, including both positive alternating-current feedback and negative direct-current feedback.

Other and further objects of my invention will appear from the following description.

BRIEF DESCRIPTION OF THE DRAWINGS

In the accompanying drawings which form part of the instant specification and which are to be read in conjunction therewith which like reference numerals are used to indicate like parts in the various views:

FIG. 1 is a schematic view showing the electrical circuitry of a preferred embodiment of my invention.

FIG. 2 is a graph showing input sound intensity as ordinate and output sound intensity as abscissa.

FIG. 3 is a front view of a protective helmet into which my personal amplifier system may be incorporated.

FIG. 4 is a left side view of the protective helmet of FIG. 3.

DESCRIPTION OF THE PREFERRED EMBODIMENT

Referring now more particularly to FIGS. 3 and 4 of the drawings, a protective helmet 6 is provided with a pair of projections adapted to receive a corresponding pair of sound attenuating earcups 8 and 108. The helmet 6 is also provided with a corresponding pair of apertures 10 and 110, which couple airborne sound to respective microphones 11 and 111 (FIG. 1). Mounted at the rear of the helmet is an electronic assembly 12, including an on-off switch 21. The sound attenuating earcups 8 and 108 are provided with respective earphones 9 and 109 (FIG. 1).

From FIGS. 3 and 4, it will be noted that aperatures 10 and 110 are positioned somewhat forwardly on the earcup receiving projections of the helmet so that sounds from in front of the wearer will provide greater outputs from the microphones than similar sounds from the rear. The microphones are thus provided with directional characteristics.

Referring now to FIG. 1, electronic assembly 12 includes a three-volt, two cell battery 20, the negative terminal of which is connected to circuit ground. The positive terminal of battery 20 is coupled through switch 21 to a B+ conductor 17. Conductor 17 is connected to the emitter of the PNP silicon junction transistor 22, the collector of which is connected to an automatic gain control (AGC) conductor 19. Conductor 17 is connected forwardly through a high resistance silicon diode 23 to the base of transistor 22, which is grounded through a 43 kilohm resistor 24. Conductor 17 is connected through a 75K resistor 36 to a bias conductor 16, which has a potential of approximately 1.3 volts. Conductor 16 is connected to one terminal of an 8.2K resistor 35, the other terminal of which is connected forwardly through high resistance diodes 34 and 33 in series to ground.

The right channel includes variable gain amplifiers 140 and 160 and further includes a constant gain amplifier 180. Similarly, the left channel includes variable gain amplifiers 40 and 60, and a constant gain differential amplifier 80. Microphone 111 is coupled through a capacitor 114 to the inputs of variable gain differential amplifier 140. The outputs of amplifier 140 are coupled to the inputs of variable gain differential amplifier 160. The outputs of amplifier 160 are connected to the inputs of differential amplifier 180. The single-ended output of amplifier 180 is connected to the base of NPN output transistor 198. Similarly, the output of amplifier 80 is connected to the base of an output transistor 98. Conductor 17 is connected through respective 0.1M biasing resistors 99 and 199 to the bases of output transistors 98 and 198. The emitters of transistors 98 and 198 are grounded; and the collectors thereof are connected through respective earphones 9 and 109 to conductor 17.

Amplifiers 140, 160 and 180 are each provided with a ground connection. The AGC conductor 19 is connected to amplifiers 140 and 160. The bias conductor 16 and the B+ conductor 17 are both coupled to amplifier 180. Conductor 17 is connected to the slider of a 50K potentiometer 37. One terminal of potentiometer 37 is coupled through a balance conductor 118 to amplifier 180.

The collector output of transistor 98 is coupled through a capacitor 26 to the anode of a diode 28, which is connected backwardly through a diode 27 to ground. The collector output of transistor 198 is coupled through a capacitor 126 to the anode of a diode 128, which is connected backwardly through a diode 127 to ground. The cathodes of diodes 28 and 128 are serially connected through a 0.1M potentiometer 30 and a 10K resistor 31 to ground. The slider of potentiometer 30 is connected to the base of a germanium junction transistor 32, the emitter of which is grounded and the collector of which is connected to AGC conductor 19. AGC conductor 19 is coupled through a capacitor 25 to ground; and the cathodes of diodes 28 and 128 are coupled through a capacitor 29 to ground.

Amplifiers 140, 160 and 180 are of similar construction to respective amplifiers 40, 60 and 80. One terminal of microphone 11 is connected to the base of a silicon transistor 42, the emitter of which is grounded. The other terminal of microphone 11 is coupled through a capacitor 14 to the base of a transistor 43, the emitter of which is grounded. AGC conductor 19 is connected to the slider of a 6K potentiometer 56. One terminal of potentiometer 56 is connected through a 36K resistor 44 to the collector of transistor 42; and the other terminal of potentiometer 56 is connected through a 36K resistor 45 to the collector of transistor 43. Conductor 19 is connected through respective 3.9M biasing resistors 46 and 47 to the bases of transistors 42 and 43. The collector of transistor 42 is connected through a 0.39M resistor 48 to the base thereof; and the collector of transistor 43 is connected through a 0.39M resistor 49 to the base thereof. The collector of transistor 42 is serially connected through a capacitor 53 and a 0.39M resistor 51 to the base of transistor 43. The collector of transistor 43 is serially coupled through a capacitor 52 and a 0.39M resistor 50 to the base of transistor 42. The collector of transistor 42 is coupled through an output capacitor 54 to the base of a transistor 63. The collector of transistor 43 is coupled through an output capacitor 55 to the base of a transistor 62.

The emitters of transistor 62 and 63 are grounded; and the collectors thereof are connected through respective 39K resistors 64 and 65 to AGC conductor 19. Amplifier 60 further includes 3.9M biasing resistors 66 and 67, 0.39M negative DC feedback resistors 68 and 69, capacitors 72 and 73, and 0.39M positive AC feedback resistors 70 and 71, which are all connected in the same manner shown for amplifier 40.

The collector of transistor 62 is coupled through an output capacitor 74 to the base of a transistor 83. The collector of transistor 63 is coupled through an output capacitor 75 to the base of a transistor 82. The emitters of transistors 82 and 83 are connected to the collector of a constant-current transistor 81, the emitter of which is grounded. The collector of transistor 82 is connected to the collector of a PNP transistor 84, the emitter of which is connected to conductor 17. The collector of transistor 83 is coupled through a 20K resistor 89 to conductor 17, and is further coupled through a capacitor 90 to the base of transistor 84. The collector of transistor 84 is coupled through a 1M resistor 91 to the base thereof. The other terminal of balance potentiometer 37 is coupled through a conductor 18 and through a 0.2M resistor 85 to the base of transistor 81. The base of transistor 81 is connected forwardly through a high resistance diode 88 to ground. The bases of transistors 82 and 83 are connected through respective 0.3M resistors 86 and 87 to bias conductor 16. The collector of transistor 82 is connected through an output capacitor 92 to the base of output transistor 98.

All transistors are of the junction type and may have a current gain, B, of 100. All transistors except 22 and 84 are of the NPN type. All transistors except 32 are formed of silicon.

Referring now to FIG. 2 which shows the AVC characteristic, for airborne sound input intensities of −30 db received by microphones 11 and 111, the resultant sound intensity provided at the ear by earphones 9 and 109 is 0 db. Similarly for airborne sound intensities of 60 db, the resulting sound intensity at the ear is 90 db. For airborne sound intensities from 60 db to 150 db, the resulting sound intensity at the ear is maintained constant at 90 db. The maximum level of sound intensity at the ear may be varied from 90 db by adjustment of potentiometer 30 to suit the particular requirements of the user.

For the silicon transistors it is assumed that the product of the dynamic resistance of the base-emitter junction and the emitter current is 52 millivolts. For germanium transistor 32 it is assumed that at 25° C. the base-to-emitter voltage is 0.23 volt at an emitter current of 100 micro-amperes and that the voltage changes by 0.1 volt for each change in emitter current by a factor of ten. For the silicon transistors it is assumed that at 25° C. the base-to-emitter voltage is 0.53 volt at an emitter current of 100 micro-amperes and that the voltage changes by 0.1 volt for each change in emitter current by a factor of ten. The high resistance silicon compensating diodes 23, 33, 34, and 88 are assumed to sustain 0.53 volt at a current of only 10 ua.

For input sound intensities less than 60 db, the circuit provides maximum gain; and the potential of AGC conductor 19 is approximately 2.7 volts. Each of transistors 42, 43, 62 and 63 has a base potential of approximately 0.5 volt; and the negative DC feedback resistors 48, 49, 68 and 69 ensure that the collector potentials are substantially equal to the base potentials. Thus, the voltage across the collector resistor of each of amplifiers 40 and 60 is 2.7−0.5=2.2 volts, which produces a current flow of 56 ua through each of the transistors of amplifiers 40 and 60. A bias current of 0.56 ua flows through each of resistors 46, 47, 66 and 67. Since the current gain is 100 for these transistors, this bias current will produce a collector current of 56 ua in each of the transistors without any current flow through DC feedback resistors 48, 49, 68 and 69. It is assumed that for all transistors the collector cutoff current is less than 0.01 ua and hence negligible.

Compensating diode 23 sustains approximately 0.6 volt; and the voltage across resistor 24 is 3−0.6=2.4 volts. A current of approximately 56 ua flows through resistor 24 of which 51 ua flows through diode 23 and 5.1 ua flows from the base of transistor 22. Accordingly, transistor 22 has the capability of providing a collector current of as much as 510 ua. However, amplifiers 40, 60, 140 and 160 draw a current of only 450 ua. Hence, transistor 22 is driven into saturation; and its collector rises to a potential of approximately 2.7 volts, which is 0.3 volt more positive than 2.4 volt potential of its base.

The collector-base junction of transistor 22 is now forwardly biased which injects a current of approximately 0.6 ua into the base region. This reduces the effective base current to $5.1-0.6=4.5$ ua which is sufficient to sustain the 450 ua drawn by the variable gain amplifiers 40, 60, 140 and 160.

Transistors 82 and 83 of differential amplifier 80 each draw a current of 50 ua; and a current of 100 ua flows through the constant-current transistor 81. The potential at the base of transistor 81 and hence the potential across diode 88 is 0.53 volt. With the slider of potentiometer 37 at its midpoint, the equivalent resistance of resistor 85 and half the resistance of potentiometer 37 is 0.225M, across which resistance appears $3-0.53=2.47$ volts. This produces a current flow of approximately 11 ua through balance conductor 18. Of this current, 10 ua flows through the compensating diode 88; and 1 ua flows into the base of transistor 81 to support its 100 ua collector current. Transistor 84 draws a collector current of 50 ua; and the base potential is 2.5 volts. The required base current of 0.5 ua flows through resistor 91, producing thereacross a drop of 0.5 volt, so that the collectors of transistors 84 and 82 have a potential of 2 volts.

The 50 ua collector current of transistor 83 produces a 1 volt drop across resistor 89, so that its collector has a potential of 2 volts. The current flow through each of biasing resistors 86 and 87 is 0.5 ua, producing a 0.15 volt drop thereacross, so that the bases of transistors 82 and 83 are at a potential of $1.3-0.15=1.15$ volts. With bias conductor 16 at a potential of 1.3 volts, 1.7 volts appears across resistor 36 producing a current flow therethrough of 22.7 ua. Of this, 2 ua flows into the bases of amplifiers 80 and 180; and 20.7 ua flows through resistor 35 producing 0.17 volt thereacross. For a current of 20.7 ua, each of compensating diodes 33 and 34 will sustain approximately 0.56 volt; and the total voltage drop across both diodes will be approximately 1.13 volts.

It is assumed that each of earphones 9 and 109 have a DC resistance of 0.1K and an AC impedance of 1K. Output transistors 98 and 198 each draw a quiescent collector current of 2.33 ma, with corresponding base potentials of approximately 0.67 volt. Each of biasing resistors 99 and 199 sustain 2.33 volts and hence pass a current of 23.3 ua, which is sufficient to support the quiescent collector current of the output transistors. This current produces a drop of 0.23 volt across the DC resistance of the earphones 9 and 109. The maximum peak value of the AC current component through the earphones is approximately 2.1 ma. The total peak current through output transistor 98 will be 2.33'0 $2.1=4.43$ ma. The base-to-emitter voltage at this peak current will be approximately 0.69 volt. The peak alternating component of current produces 2.1 volts across the 1K, AC impedance of the earphones. The sum of the DC and AC components of voltage across earphone 9 is $0.23+2.1=2.33$ volts. The minimum collector voltage of transistor 98 is thus $3-2.33=0.67$ volt. Output transistor 98 is driven slightly into the saturation region, since its base-collector junction is forwardly biased by approximately 0.02 volt. There is negligible distortion, however, since the incremental resistance of the base-collector junction is extremely high at such small values of forward bias. It may be noted that even if the base-collector junction of transsistor 98 were forwardly biased by 0.26 volt, a current of only 0.2 ua would be ejected from the base region of transistor 98; and with a peak AC input base current of 21 ua from amplifier 80, the distortion would be only 1%. For negative going inputs from amplifier 80, the minimum collector current of output transistor 98 is $2.33-2.1=0.23$ ma. Thus, the output transistors operate class A and are not driven excessively close to cutoff.

Components 26, 27 and 28 tend to provide across capacitor 29 a voltage in accordance with the peak-to-peak AC voltage swing at the collector of output transistor 98. Components 126, 127 and 128 tend to provide across capacitor 29 a voltage in accordance with the peak-to-peak AC voltage swing at the collector of output transistor 198. Diodes 28 and 128 of these peak-to-peak detectors also serve as an OR circuit. Thus, capacitor 29 is charged to a positive voltage in accordance with the greater output of the two peak-to-peak detectors.

When the potential at the slider of potentiometer 30 and hence at the base of transistor 32 rises to 0.23 volt, transistor 32 draws a collector current of 110 ua; and the potential of AGC conductor 19 drops to 2.4 volts, which is the same as that of the edge of saturation region, since the potential difference across the collector-base junction of transistor 22 is zero. Transistor 22 now provides a collector current of 510 ua. The current flow through transistors 42, 43, 62 and 63 of the variable gain amplifiers 40, 60, 140 and 160 is reduced from 56 ua to 50 ua; and the total current drawn by the variable gain amplifiers is 400 ua. This reduces the gain of each of the variable gain amplifiers by only 11% or 1 db; and the gains of each of left and right channels are accordingly reduced by only 2 db. If the potential at the slider of potentiometer 30 and hence at the base of transistor 32 were to approach 0.3 volt, then nearly the entire 510 ua collector current of transistor 22 would be diverted to ground through transistor 32; and the potential of AGC conductor 19 would be 0.3 volt. The current flow through each of transistors 42, 43, 62 and 63 of the variable gain amplifiers would be reduced by a factor of 100 to 0.56 ua; and the gains of the variable gain amplifiers would be drastically reduced. Accordingly, it will be appreciated that the AGC system regulates with the base of transistor 32 at a potential in the region of approximately 0.23 volt to 0.3 volt. The maximum sound output intensity of earphones 9 and 109 may readily be set between 82 db and 98 db by adjustment of the slider of potentiometer 30.

The maximum peak-to-peak AC output at the collectors of transistors 98 and 198 is 4.2 volts. Diodes 27, 28, 127 and 128 are preferably germanium and may each cause a loss of 0.2 volt in the rectified output across capacitor 29. Accordingly, the maximum voltage across capacitor 29 will be 3.8 volts. With the slider of potentiometer 30 moved upwardly to its extreme limit, a maximum sound output of 98 db will result for inputs exceeding 68 db. The slider voltage is $10/110=0.091$ of that across capacitor 29, and hence is $3.8 (0.091)=0.346$ volt, neglecting the base current drawn by transistor 32. The slider output resistance is 9.1K; and the base current drawn by transistor 32 is 5.1 ua. This reduces the slider potential by 0.046 volt to 0.3 volt.

With the slider of potentiometer moved downwardly to its extreme limit, a maximum sound output of 82 db will result for inputs exceeding 52 db. The peak-to-peak AC output at the collectors of transistor 98 and 198 will be 0.7 volt; and the rectified output across capacitor 29 will be 0.3 volt. This is equal to the slider voltage since the slider output resistance is now substantially zero. It will be appreciated that if transistor 32 is driven into the saturation region, the potential of AGC conductor 19 will decrease below 0.3 volt. For example, if the potential of conductor 19 is 0.2 volt, the collector-base junction of transistor 32 will be forwardly biased by 0.1 volt. This causes a current of 5 ua to be ejected from the base region. The 510 ua collector current of transistor 32 will however be sustained if its base current from the slider of potentiometer 30 is increased by 5 ua from 5.1 ua to 10.1 ua. This requires a negligible increase in the base potential of transistor 32 which remains substantially 0.3 volt. With AGC conductor 19 at 0.2 volt, the currents drawn by the transistors of variable gain amplifiers 40 and 60 would be reduced by a factor of 1000 to 0.056 ua; and the gains would be further reduced.

The quiescent operating point of transistor 42 is stabilized by feedback resistor 48 at a base-collector junction potential of substantially zero. Resistor 48 provides degeneration at all frequencies. While this degeneration does stabilize the operating point, it severely lowers the input impedance of amplifier 42 and reduces the range over which the gain of the amplifier can be varied. Resistor 50 in conjunction with capacitor 52 provides regenerative feedback for all frequencies except very low frequencies approaching zero. It will be noted that the resistance values of resistors 48 and 50 are the same. Assuming that the amplifier 40 is reasonably well balanced, the degenerative current through resistor 48 will be neutralized by the regenerative current through resistor 50, for signal frequencies greater than zero, so that there will be no net feedback current into the base of transistor 42. In a similar fashion, resistor 51 in conjunction with capacitor 53 compensates for the degenerative feedback provided by resistor 49 for all signal frequencies greater than zero.

The positive AC feedback through resistors 50 and 51 also tends to keep the outputs at the collectors of amplifiers 42 and 43 substantially the same in magnitude but opposite in polarity. Suppose for example that an input is applied only to the base of transistor 42; and no input is applied to the base of transistor 43. The collector output of transistor 42 will nevertheless be coupled through capacitor 53 and resistor 51 into the base of transistor 43. The amplifier including transistor 43 now functions substantially as a unity-gain inverting amplifier, producing at its collector a potential opposite in polarity and nearly equal in amplitude to that at the collector of transistor 42. Similarly, if an input were applied only to the base of transistor 43, then the collector output of transistor 43 would be coupled through capacitor 52 and resistor 50 to the base of transistor 42, thereby producing at its collector a potential opposite in polarity and nearly equal in magnitude to that at the collector of transistor 43. It will be appreciated that since the output of microphone 11 is applied between the bases of transistors 42 and 43, the inputs to these transistors are well balanced initially.

For a collector current of 56 ua, the emitter resistance of transistor 42 will be 52 mv/56 ua=0.93K. The minimum base input resistance of transistor 42 and of transistor 63 is hence 93K. If the slider of potentiometer 56 is at its midpoint, the equivalent resistance of collector resistor 44 and half the resistance of potentiometer 56 is 39K. Since the collector of transistor 42 is further loaded by resistors 48 and 51 as well as the base input resistance of transistor 63, the total collector load resistance of transistor 42 is 24K; and the maximum voltage gain of amplifier 40 is 24/0.93=26. If the voltage on AGC conductor 19 is sufficiently reduced that the current through transistor 42 is only 5.6 ua, the emitter resistance of transistor 42 will increase to 9.3K; and its base input resistance as well as that of transistor 63 will increase to 930K. The equivalent collector load resistance of transistor 42 is now 31K; and the voltage gain of amplifier 40 is 31/9.3=3.4. If the voltage on AGC conductor 19 is further reduced such that the current through transistor 42 is only 0.56 ua, the emitter resistance of transistor 42 will increase to 93K; and its base input resistance, as well as that of transistor 63 will increase to 9.3M. The equivalent collector load resistance of transistor 42 is now 32K; and the voltage gain of amplifier 40 is 32/93=0.35.

With a collector current of 50 ua for each of transistors 82 and 83, the emitter resistance of each of these transistors will be 52 mv/50 ua=1K. The base input resistance of transistors 82 and 83 is hence 100K. Since the collector of transistor 63, for example, is loaded not only by its collector resistance 65 but further by resistors 69, 70 and 86, as well as the base input resistance of transistor 82, the equivalent collector load resistance of transistor 63 is 23K; and the maximum voltage gain of amplifier 60 is 23/0.93=25. If the voltage on AGC conductor 19 is sufficiently reduced that the current through transistor 63 is only 5.6 ua, the emitter resistance of transistor 63 will increase to 9.3K; and the gain of amplifier 60 will be reduced to 23/9.3=2.5. If the voltage on AGC conductor 19 is further reduced so that the current through transistor 63 is only 0.56 ua, the emitter resistance of transistor 63 will increase to 93K; and the gain of amplifier 60 will be reduced to 23/93=0.25.

Since the quiescent collector current of transistor 98 is 2.33 ma, its emitter resistance is 52 mv/2.33 ma=22 ohms. The base input resistance of amplifier 98 is accordingly 2.2K. To provide a maximum peak AC collector current of 2.1 ma in transistor 98 requires a corresponding peak AC base current of 21 ua. This requires peak AC signals of only 1.2 mv at the bases of transistors 82 and 83. Since the emitter resistance of transistors 82 and 83 is 1K at a quiescent collector current of 50 ua, the 1.2 mv peak AC base inputs will produce peak AC collector currents of 1.2 ua in transistors 82 and 83. The base input resistance of transistor 84 is 100K; and the total equivalent collector load resistance of transistor 83 is hence reduced from 20K to 16.7K. The peak AC base input voltage of transistor 84 is thus (1.2 ua)(16.7K)=20 mv. Since the emitter resistance of transistor 84 is also 1K, its peak AC collector current is 20 ua. The polarities are such that the AC collector currents of transistors 82 and 84 are additive because of their cascode, or DC pushpull, connection. Thus, the total peak AC current from the collectors of transistors 82 and 84 is 21 ua.

Amplifier 80 in actuality has two amplifying stages, each providing gain. The first stage includes transistors 82 and 83 which provide an output across resistor 89; and the second stage includes transistor 84 which drives the base input resistance of output transistor 98. Although the two stages of amplifier 80 as well as output transistor 98 are connected in series and although all three amplifying stages are supplied from conductor 17 without any decoupling, there results no motorboating oscillation.

Amplifiers 40 and 60 are decoupled from conductor 17 by the collector resistance of transistor 22 and by capacitor 25. Since 40 and 60 are balanced differential amplifiers, no motorboating oscillation would occur even if three such amplifiers were provided instead of only two.

The current gains of amplifiers 80 and 180 are proportional to their quiescent collector currents and hence proportional to the collector current of the constant current transistor 81. This collector current is in turn proportional to the current through compensating diode 88 and hence through the balance conductors 18 and 118. By moving the slider of potentiometer 37 from its midpoint, the gains of amplifiers 80 and 180 may be differentially varied to suit the requirements of the individual user. Thus, difference in the apparent intensities of sound at the left and right ears may be equalized, so that a source of sound may be properly localized. For example, if sound from a source directly ahead of the user appears to come from a direction slightly to the left, then the slider of potentiometer 37 should be moved somewhat to the right. This decreases the current through conductor 18 and hence decreases the gain of left channel amplifier 80, and simultaneously increases the current through balance conductor 118 and hence increases the gain of right channel amplifier 180.

If a sudden an extremely intense sound occurs to the left of the dead ahead position, such that the sound intensity in earphone 9 is 6 db greater than that in earphone 109, than the output from detector 26-27-28 will be twice that from detector 126-127-128. The output voltage across capacitor 29 will thus be governed by the greater output of the detector for the left channel. Transistor 32 will be rendered conductive and discharge capacitor 25 sufficiently to reduce the voltage on AGC conductor 19, so that the sound from the left earphone 9 will not exceed 90 db. Since the gain reduction in amplifiers 40 and 60 of the left channel is matched to within 1 db of the gain reduction in amplifiers 140 and 160 of the right channel, the sound intensity in the right earphone 109 will be substantially 84 db. Thus the differential variation in sound intensities between the left and right channels is preserved because of the similar reductions in gain in both channels, and the location of the intense sound source may readily be determined by the user. If the intense sound ceases, then capacitor 25 will be gradually recharged through transistor 22 to increase the voltage on AGC conductor 19 and thus synchronously increase the gains of both channels.

The discharge of capacitor 25 through transistor 32 may be extremely rapid, while the charging of capacitor 25 through transistor 22 will be relatively slower. In conventional AGC systems, a sudden reduction of gain can produce extraneous transient electrical pulses of an amplitude exceeding the desired signal representing the amplified output of the sound receiving microphone. The magnitude of these extraneous transients is proportional to the rate of reduction in gain. In conventional AGC systems, the gain reduction may be fairly fast but it cannot be instantaneous. However, in my system, variation in gain produces no extraneous transients; and the rate of reduction in gain may be so rapid as to be substantially instantaneous.

Each of amplifiers 40 and 60 is biased at the knee of the collector characteristic which is at the edge of the saturation region, so that there is substantially no voltage across the collector-base junction. The voltages across capacitors 14, 52, 53, 54, 55, 72, and 73 are substantially zero. This is true irrespective of the magnitude of the voltage on AGC conductor 19. It will be appreciated that conductor 19 provides a variable B+ supply to the variable gain amplifiers of both channels.

Large variations in the voltage of conductor 19 produce relatively small variations in the substantially common voltage at the bases and collectors of transistors 42, 43, 62, and 63. The voltage at these bases and collectors changes by only 0.1 volt for each change by a factor of ten in the collector currents. With the voltage on AGC conductor 19 varying from 2.7 volts to 0.3 volt, the voltage of the bases and collectors of the transistors of amplifiers 40 and 60 vary from only 0.5 volt to 0.3 volt. If the voltage on AGC conductor 19 is instantaneously changed from 2.7 volts to 0.3 volt, momentary negative going pulses of 0.2 volt amplitude will be coupled through capacitors 75 and 74 to the bases of transistors 82 and 83. However, no change results in the collector current of constant current transistor 81; and the potential at the collectors of transistors 82 and 84 remains constant, so that no extraneous pulse is applied to the base of output transistor 98.

Amplifiers 40, 60, and 80 are balanced amplifiers; and no extraneous pulse will be coupled to the base of output transistor 98 if the balance can be made substantially perfect. This is the purpose of potentiometer 56 of amplifier 40. Potentiometer 56 may be adjusted by the following procedure. A low output impedance signal generator may be connected between conductor 19 and ground. The signal generator may be set at a convenient frequency such as 1 KHz and the amplitude conveniently set for a 1 volt peak-to-peak variation in the potential of conductor 19. A millivoltmeter may be connected between the collector of transistor 98 and ground. Potentiometer 56 may now be adjusted until the output of the millivoltmeter is a minimum.

It will be understood that amplifier 140 also includes a corresponding potentiometer 156 (not shown). After the adjustment of potentiometer 56, the millivoltmeter may be reconnected between the collector of output transistor 198 and ground. Potentiometer 156 of amplifier 140 may now be adjusted until the output of the millivoltmeter is a minimum.

Potentiometers 56 and 156 should be adjusted at the factory; and the only adjustments permitted to the user are of amplitude, by potentiometer 30, and of balance, by potentiometer 37. The factory adjustments of potentiometers 56 and 156 are preferably made with balance potentiometer 37 at its midpoint.

It will be seen that I have accomplished the objects of my invention. Sound attentuating ear defenders ideally exclude all airborne sound and permit only electrically reproduced sound to be heard. The gains of the left and right amplifying channels are synchronously varied over a wide range, while preserving an extremely small range of differential variation by controlling the variable B+ supply of the variable gain amplifiers on AGC conductor 19. The gains of both channels are synchronously varied in response to the greater of the output signals of the two channels. Each variable gain amplifier comprises a balanced, collector-coupled differential transistor amplifier biased with substantially zero voltage across the collector-base junction. Operating point stability is ensured by negative DC feedback; and adverse degenerative effects are compensated for by positive AC feedback. My system is provided with factory adjustments to ensure substantially perfect differential balance for the amplifiers of both the left channel and the right channel so that no extraneous transients are produced in the earphones as a result of changes in the AGC voltage. Accordingly, the AGC system may have substantially instantaneous response to sudden high intensity sound and to high intensity sound pulses. My amplifier system is provided with user adjustments for both maximum sound output and for balance between the left and right channels.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention, what I claim is:

1. A personal amplifier system including in combination a pair of microphones, a pair of earphones, means including a first variable gain amplifier providing an output for coupling one microphone to one earphone, means including a second variable gain amplifier providing an output for coupling the other microphone to the other earphone, and means selectively responsive to that one of the amplifiers providing the greater output for varying the gains of the first and second amplifiers.

2. A personal amplifier system including in combination a pair of microphones, a pair of earphones, means including a first and a second variable gain amplifier for coupling one microphone to one earphone, means including a third and a fourth variable gain amplifier for coupling the other microphone to the other earphone, the first and third amplifiers having substantially the same first range of gain variation, the second and fourth amplifiers having substantially the same second range of gain variation, each amplifier having a maximum gain much greater than unity, and means responsive to at least one of the second and fourth amplifiers for producing substantially identical variations in gain of the first and third amplifiers throughout the first range and for producing substantially identical variations in gain of the second and fourth amplifiers throughout the second range.

3. A system as in claim 2 wherein each microphone is provided with a directional characteristic.

4. A system as in claim 2 further including a pair of ear defenders, each earphone being mounted within a corresponding ear defender.

5. A system as in claim 2 further including a pair of ear defenders, each microphone being mounted in proximity to a corresponding ear defender.

6. A personal amplifier system including in combination a pair of microphones, a pair of earphones, a pair of similar transistors each having a base and an emitter and a collector, means connecting the emitters to a point of reference potential, means coupling each microphone to the base of a corresponding transistor, a source of variable potential, means including a pair of similar resistors for coupling the source to the collectors, means coupling each collector to a corresponding earphone, and means responsive to at least one of the collectors for varying the potential of the source.

7. A system as in claim 6 further including means for biasing each transistor to a substantially zero voltage differential between base and collector.

8. A system as in claim 6 further including means for biasing each transistor to a substantially zero voltage differential between base and collector, said biasing means including means comprising a second pair of similar resistors for coupling the source to the bases.

9. A system as in claim 6 further including means for biasing each transistor to a substantially zero voltage differential between base and collector, said biasing means including means comprising a second pair of similar resistors for connecting the collector of one transistor to the base thereof and for connecting the collector of the other transistor to the base thereof.

10. A personal amplifier system including in combination a pair of microphones, a pair of earphones, a pair of similar transistors each having a base and an emitter and a collector, means connecting the emitters to a point of reference potential, means coupling each microphone to the base of a corresponding transistor, a source of potential, a constant current device having two terminals, means connecting the source to a first terminal, means including a pair of similar resistors for connecting the collectors to the second terminal, means coupling each collector to a corresponding earphone, a third transistor having a collector, means connecting the second terminal to the collector of the third transistor, and means responsive to the collector of at least one of the pair for controlling the collector current of the third transistor.

11. A personal amplifier system including in combination a pair of microphones; a pair of earphones; a source of variable potential; a pair of variable gain amplifiers; each amplifier comprising a pair of similar transistors each having a base and an emitter and a collector, means connecting the emitters to a point of reference potential, means including a first pair of similar resistors for connecting the collectors to the source, means including a second pair of similar resistors for connecting the collector of one transistor to the base thereof and for connecting the collector of the other transistor to the base thereof, and means including a third pair of similar resistors for connecting the collector of one transistor to the base of the other and for connecting the base of said one transistor to the collector of said other; means connecting each microphone between the bases of a corresponding amplifier; means coupling the collectors of each amplifier to a corresponding earphone; and means responsive to the collectors of at least one amplifier for varying the potential of the source.

12. A personal amplifier system including in combination a pair of microphones; a pair of earphones; a source of variable potential; a pair of variable gain amplifiers; each amplifier comprising a first pair of similar transistors each having a base and an emitter and a collector, means connecting the emitters to a point of reference potential, means including a pair of similar resistors for connecting the collectors to the source, a second pair of similar transistors each having a base and an emitter and a collector, a constant current device, means connecting the emitters of the second pair to the device, and means coupling each collector of the first pair to a corresponding base of the second pair; means connecting each microphone between the bases of the first pair of transistors of a corresponding amplifier; means coupling at least one collector of the second pair of transistors of each amplifier to a corresponding earphone; and means responsive to at least one collector of the second pair of transistors of at least one amplifier for varying the potential of the source.

* * * * *